US008958860B2

(12) United States Patent
Banerjee et al.

(10) Patent No.: US 8,958,860 B2
(45) Date of Patent: Feb. 17, 2015

(54) OPTICAL SENSORS FOR INTRAOPERATIVE PROCEDURES

(75) Inventors: Saumya Banerjee, Hamden, CT (US); Joshua Benjamin Stopek, Yalesville, CT (US); Timothy Sargeant, Guilford, CT (US)

(73) Assignee: Covidien LP, Mansfield, MA (US)

( * ) Notice: Subject to any disclaimer, the term of this patent is extended or adjusted under 35 U.S.C. 154(b) by 945 days.

(21) Appl. No.: 13/091,519

(22) Filed: Apr. 21, 2011

(65) Prior Publication Data

US 2011/0282170 A1    Nov. 17, 2011

Related U.S. Application Data

(60) Provisional application No. 61/345,414, filed on May 17, 2010.

(51) Int. Cl.
*A61B 5/1455* (2006.01)
*A61B 5/00* (2006.01)
*A61B 19/00* (2006.01)
*A61B 17/072* (2006.01)
*A61B 17/115* (2006.01)
*A61B 17/29* (2006.01)
*A61B 17/00* (2006.01)

(52) U.S. Cl.
CPC ........... *A61B 5/0059* (2013.01); *A61B 5/14552* (2013.01); *A61B 5/0084* (2013.01); *A61B 5/6833* (2013.01); *A61B 5/6846* (2013.01); *A61B 5/6876* (2013.01); *A61B 5/6884* (2013.01); *A61B 17/07207* (2013.01); *A61B 17/1155* (2013.01); *A61B 17/29* (2013.01); *A61B 19/46* (2013.01); *A61B 2017/00057* (2013.01); *A61B 2017/00544* (2013.01); *A61B 2017/2927* (2013.01); *A61B 2019/521* (2013.01); *A61B 2562/164* (2013.01)
USPC ........................................... 600/344; 600/323

(58) Field of Classification Search
CPC ............. A61B 5/1455; A61B 5/14551; A61B 5/14552; A61B 2562/00; A61B 2561/02; A61B 2562/0233; A61B 2562/16; A61B 2562/164
USPC .................. 600/310, 322, 323, 341, 344
See application file for complete search history.

(56) References Cited

U.S. PATENT DOCUMENTS

| 5,131,391 | A | * | 7/1992 | Sakai et al. | 600/334 |
| 5,438,987 | A | | 8/1995 | Thacker et al. | |
| 5,715,816 | A | * | 2/1998 | Mainiero et al. | 600/323 |
| 5,807,261 | A | | 9/1998 | Benaron et al. | |
| 5,833,603 | A | | 11/1998 | Kovacs et al. | |
| 5,995,860 | A | * | 11/1999 | Sun et al. | 600/322 |
| 6,134,458 | A | | 10/2000 | Rosenthal | |
| 6,290,713 | B1 | | 9/2001 | Russell | |
| 6,802,812 | B1 | | 10/2004 | Walker et al. | |
| 6,811,563 | B2 | | 11/2004 | Savage, Jr. et al. | |
| 7,149,562 | B2 | | 12/2006 | Walker et al. | |
| 7,189,961 | B2 | | 3/2007 | Johnston et al. | |
| 7,500,954 | B2 | * | 3/2009 | Wilser et al. | 600/467 |
| 7,544,166 | B2 | * | 6/2009 | Yuan et al. | 600/467 |

(Continued)

*Primary Examiner* — Eric Winakur

(57) ABSTRACT

An intra-operative sensor device for detecting tissue or body parameters includes one or more light emitting sources and one or more photo-detectors. An optical isolator ring may be placed around either the one or more light emitting sources or around the one or more photo-detectors. The intra-operative sensor device may be a stand alone device or may be operatively coupled into a surgical instrument, such as a laparoscopic device.

9 Claims, 3 Drawing Sheets

(56) References Cited

U.S. PATENT DOCUMENTS

| | | |
|---|---|---|
| 7,603,153 B2 | 10/2009 | Jacobsen et al. |
| 2004/0236192 A1 | 11/2004 | Necola Shehada et al. |
| 2005/0033556 A1 | 2/2005 | Miura |
| 2005/0215895 A1* | 9/2005 | Popp et al. .............. 600/437 |
| 2008/0221409 A1 | 9/2008 | Hoarau |
| 2009/0137876 A1 | 5/2009 | Brophy |
| 2010/0087782 A1 | 4/2010 | Ghaffari et al. |

* cited by examiner

OPTICAL SENSORS FOR INTRAOPERATIVE PROCEDURES

This application claims priority from provisional application Ser. No. 61/345,414, filed May 17, 2010, the entire contents of which are incorporated herein by reference.

BACKGROUND

1. Technical Field

The present disclosure relates to devices and methods of using devices to monitor conditions within a body cavity, and more particularly to optical sensors and methods of using optical sensors during a surgical procedure to monitor the physical condition of the surgical site.

2. Background of Related Art

During or after a surgical procedure, the physical conditions of the surgical site might need to be monitored. The early detection of complications during or after a surgical procedure may facilitate a timely therapeutic response prior to the onset of irreversible damage. For example, the presence of certain particulates or contaminants may complicate a procedure. In addition, the lack of sufficient vascularization at the tissue site may disrupt adequate oxygen circulation to the tissue. A lack of oxygen circulation to the tissue may endanger the function and survival of tissue.

Various devices and methods to monitor the conditions of a surgical site have been employed. For example, a photopelythysmograph (PPG) is a device that optically measures the amount of blood in a part of the body. For example, the PPG measures the amount of light passing through a patient's finger by placing a light source on one side of the finger and a light sensitive resistor on the other side. By monitoring the variations in resistance of the light sensitive resistor, the PPG can optically capture the pulsation and oxygen saturation of the arterial blood flow.

The accuracy of the data collected, using such devices and methods, is limited by the configuration of the sensors used and the placement of the sensors in relation to the surgical site. Disturbances, including a patient's motion and ambient lighting, may distort the measurements collected by the sensors.

SUMMARY

The present disclosure describes an optical sensor for intra-operative procedures and methods for using the optical sensor.

In one aspect, an intra-operative sensor device for detecting tissue or body parameters includes a sensor including one or more light emitting sources and one or more photo-detectors, wherein an optical isolator ring is placed around either the one or more light emitting sources or the one or more photo-detectors.

The sensor may include light emitting sources and photo-detectors that are arranged in different configurations. In a first configuration, the one or more light emitting sources is placed within the optical isolator ring, and the one or more photo-detectors radially surround the optical isolator ring and the one or more light emitting sources that are placed within the optical isolator ring. In a second configuration, the one or more photo-detectors is placed within the optical isolator ring, and the one or more light emitting sources radially surround the optical isolator ring and the one or more photo-detectors that are placed within the optical isolator ring.

In one embodiment, the intra-operative sensor device may be operatively coupled to a member which is adapted and configured to transition between a furled state and an unfurled state. In one embodiment, the member is an inflatable sleeve and a hose may be operatively coupled to the inflatable sleeve to provide inflation fluid. In the unfurled state, the inflatable sleeve may be inserted into an incision and placed adjacent a tissue. By reducing the pressure in the inflatable sleeve, the inflatable sleeve will transition to the furled state and may be wrapped around the adjacent tissue.

The intra-operative sensor device may be operatively coupled into a laparoscopic device. The sensor may be operatively coupled to the distal end of an elongated shaft of the laparoscopic device. In an embodiment, the laparoscopic device may include an elongated shaft having a distal end, and an end effector including first and second jaw members. A light emitting source may be operatively coupled into the first jaw member; a photo-detector may be operatively coupled into the second jaw member.

In another aspect, the present disclosure provides an intra-operative sensor device for detecting tissue or body parameters comprising a photo-detector and a plurality of light emitting sources spaced radially from the photo detector. The photo-detector detects light backscattered from the light emitted by the light emitting source to detect parameters of the tissue or body. In one embodiment, the light emitting source substantially encircles the photo-detector. An optical isolator ring can be positioned between the photo-detector and the plurality of light emitting sources.

In another aspect, an intra-operative sensor device for detecting tissue or body parameters is provided comprising a light emitting source and a plurality of photo-detectors spaced radially from the light emitting source. The photo-detector detects light backscattered from the light emitted by the light emitting sources to detect parameters of the tissue or body. In one embodiment, the photo-detectors substantially encircle the light emitting source. An optical isolator ring can be positioned between the plurality of photo-detectors and light emitting source.

These and other embodiments of the present disclosure will be described in greater detail with reference to the appended figures.

BRIEF DESCRIPTION OF THE DRAWINGS

By way of description only, embodiments of the disclosure will be described with reference to the accompanying drawings, in which.

DETAILED DESCRIPTION

Figure 1:
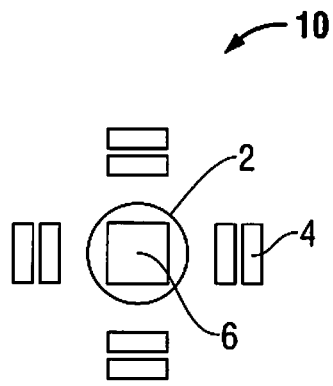
FIG. 1 illustrates an intra-operative sensor including a first configuration of light sources and photo-detectors in accordance with an embodiment of the present disclosure.

Particular embodiments of the present disclosure will be described herein with reference to the accompanying drawings. As shown in the drawings and as described throughout the following descriptions, and is traditional when referring to the relative positioning on an object, the term "proximal" refers to the end of the apparatus that is closer to the user and the term "distal" refers to the end of the apparatus that is further from the user. In the following description, well-known functions or constructions are not described in detail to avoid obscuring the present disclosure in unnecessary detail.

The intra-operative sensors described herein function by collecting reflected and/or backscattered light of varying wavelengths and processing the information collected to identify the physiological condition of the tissue being operated upon or the conditions within the body cavity, including, but not limited to, clearance and/or absorption of, for example, specific particulates, oxygen saturation, or contaminants. The intra-operative sensors can also identify leaks. The sensors could also identify lack of vascularization at the tissue site. For example, the application of the intra-operative sensors disclosed herein can range from checking for gastrointestinal leaks, where vascularization at the site of anastomosis is critical to healing, to checking oxygen saturation in burn victims to determine any compromise in the healing process.

Depending upon the particular application, an intra-operative sensor may include a particular configuration of photo-detectors and light emitting sources. A first and a second embodiment of an intra-operative sensor 10, 20 include different configurations of photo-detectors 6 and light emitting sources 4 and will now be described with reference to FIGS. 1 and 2.

The first embodiment of an intra-operative sensor 10, as shown in FIG. 1, includes a photo-detector 6 around which multiple light emitting sources 4 are placed (more than one photo-detector could also be provided). The light emitting sources 4 may be placed radially around the one or more photo-detectors 6. In the embodiment shown, the light emitting sources 4 substantially encircle the photo detector(s) 6. In addition, the light emitting sources 4 may be spaced equidistantly apart from one another. Other spacings are also contemplated. The light emitting sources 4 may include, but are not limited to, light emitting diodes (LED's).

An optical isolator ring 2 may be placed around the one or more photo-detectors 6. In this manner, the ring 2 is between the detector(s) 6 and light emitting sources 4. The optical isolator ring 2 inhibits direct interference from light emitting sources or from ambient light, i.e., the ambient light of the operating room. By reducing the interference from light sources other than the light emitting sources 4, the accuracy of measurements collected by the photo-detectors 6 may be enhanced.

Figure 2:
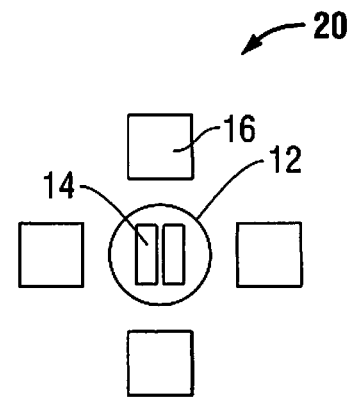
FIG. 2 illustrates an intra-operative sensor including a second configuration of light sources and photo-detectors in accordance with another embodiment of the present disclosure.

In a second embodiment of FIG. 2, intra-operative sensor 20 includes a configuration of photo-detectors 16 and light emitting sources 14, in which multiple photo-detectors 16 are placed radially around one or more light emitting sources 14. The photo-detectors 16 may be placed radially around the one or more light emitting sources 14. In the embodiment shown, the photo-detectors 16 substantially encircle the light emitting sources 14. In addition, the photo-detectors 16 may be placed equidistantly from one another, although other spacings are also contemplated. The placement of multiple photo-detectors 16 around light emitting sources 14 facilitates an accurate spot-check measurement of the tissue. An optical isolator ring 12 may be placed around the one or more light emitting sources 14. In this manner, ring 12 is between light emitting sources 14 and detector(s) 16, and as described above, this placement of the optical isolator ring 12 inhibits unwanted interference from light sources other than light emitting sources 14.

The light emitting sources 4, 14 may be matched to a particular wavelength and may also be modulated to allow for selective signal detection. Moreover, the intra-operative sensors may include a plurality of light emitting sources 4, 14, in which the light emitting sources are configured and adapted to radiate a plurality of wavelengths into a tissue site. The photo-detectors 6, 16 are configured to receive the light radiated by the light emitting sources after absorption of the light by the substance, e.g., tissue or blood, through which the light was radiated. In addition, the photo-detector 6, 16 may provide a constant feedback to provide information about the substance, such as a tissue or fluid through which the light from the light emitting source 4, 14 traveled.

The intra-operative sensors 10, 20 described herein function by collecting reflected and/or backscattered light of varying wavelengths. A processing unit interprets the data collected to identify the physiological condition of the tissue being operated upon or the conditions within the body cavity, including, but not limited to, clearance and/or absorption of, for example, specific particulates, oxygen saturation, or contaminants.

The intra-operative sensors 10, 20 can also identify leaks and lack of vascularization at the tissue site. For example, the application of the intra-operative sensors disclosed herein can include checking for gastrointestinal leaks, where vascularization at the site of anastomosis is critical to healing. It can also include checking oxygen saturation in burn victims to determine any compromise in the healing process.

In the FIG. 1 embodiment, the photo-detector is placed in the center with multiple light sources surrounding it. In this way, calculations of an average over a specific area are performed. That is, an average measurement of the tissue surface area covered by the light-emitting source is calculated. In the embodiment of FIG. 2, with the light source in the center encircled by photo-detectors, detailed spot check measurements of tissue are provided.

Intra-operative sensors 10, 20 may be employed as stand alone instruments or may be operatively coupled to a surgical instrument, such as, device for open surgery or an arthroscopic or laparoscopic device, e.g., a grasper. In addition, the intra-operative sensors 10, 20 may be operatively coupled to any device that passes through small incisions or through a port placed within an incision during a minimally invasive surgical procedure.

Figure 2A:
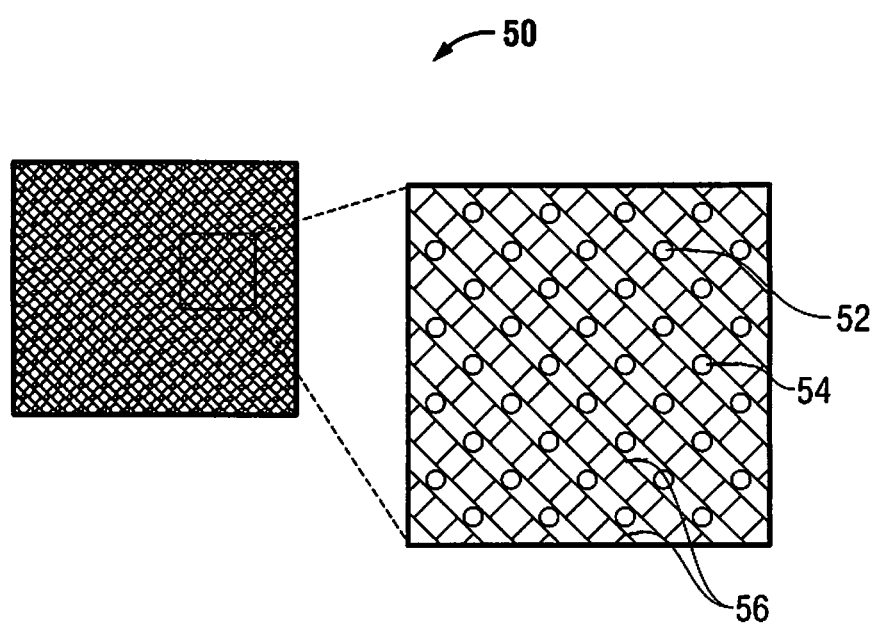
FIG. 2A illustrates another embodiment of the sensor arrangement of the present disclosure.

In the alternate embodiment of FIG. 2A, a flexible patch 50 has a mesh-like structure 56 which is made of an optical isolator that prevents contamination of the received signal from ambient or refracted light from adjacent emitters. As shown schematically, photo-detectors are designated by reference numeral 52 and light emitting sources are designated by reference numeral 54, separated by mesh 56. As with the other embodiments, this arrangement will display parameter such as oxygenation, CO/CO2 levels and/or contaminant presence. The intra operative sensor of FIG. 2A can be used as a stand alone instrument or operatively coupled to a surgical instrument.

Examples of devices incorporating intra-operative sensors, e.g., intra-operative sensors 10, 20, will now be described with reference to FIGS. 3-6. An intra-operative sensor device 100 will now be described with reference to FIGS. 3-3A. The intra-operative sensor device 100 generally includes an inflatable sleeve 108 on which one or more light emitting sources 104 and one or more photo-detectors 106 are mounted. An optical isolator ring 102 may be placed around either the one or more light emitting sources 104 or the one or more photo-detectors 106, and in the illustrated embodiment of FIG. 3, the optical isolator ring 102 is placed around the photo detectors 106.

Figure 3:
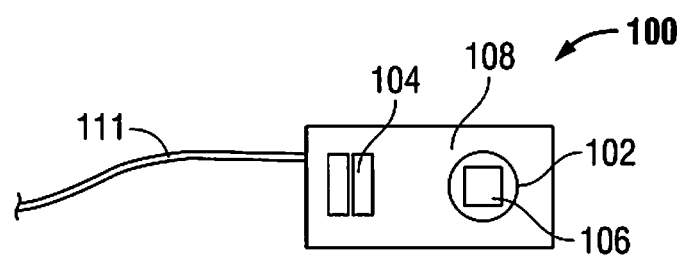
FIG. 3 is a top view of an intra-operative sensor device shown in a first state in accordance with an embodiment of the present disclosure.
Figure 3A:
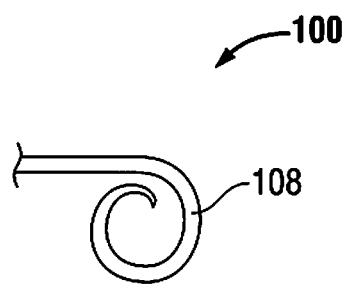
FIG. 3A is a side view of the intra-operative sensor device of FIG. 3 shown in a second state.

The inflatable sleeve 108 is configured and adapted to transition between a furled state (FIG. 3A) and an unfurled state (FIG. 3). To facilitate this transition, a hose or conduit 111 may be operably coupled to the inflatable sleeve 108 to provide inflation fluid. The inflatable sleeve 108 may have a generally rectangular shape and may be biased to transition to one of the furled and unfurled states in the absence of pressure provided to the inflatable sleeve 108 in the form of inflation fluid. For example, in the absence of inflation pressure, the inflatable sleeve 108 may transition to the furled, i.e., rolled, state (FIG. 3A). It is to be understood, that the inflatable sleeve 108 may define other geometric shapes or configurations. For example, inflatable sleeve 108 may have a triangular, diamond, circular, or non-symmetrical shape. One skilled in the art may envision other configurations for the inflatable sleeve 108. The sleeve 108 provides an increased surface area to enable provision of a larger number of sensors. It can also provide measurements over different areas of tissue due to its size (length/width) and can provide real time information on the tissue surface area. Providing plots of saturation or other parameters is also contemplated.

The intra-operative sensor device 100 may be wrapped around tissue. As the intra-operative sensor device 100 is inflated, it unrolls and extends to the unfurled state (FIG. 3). In the unfurled state, the intra-operative sensor device 100 may be placed adjacent a tissue. As the inflation pressure is lessened, the intra-operative sensor device 100 will transition back to the furled or rolled state, and will become wrapped around the tissue upon which the intra-operative sensor device 100 was placed. It is to be understood that the inflation of the inflatable sleeve 108 may be accomplished by using a gas or a liquid.

In other embodiments, instead of an inflatable sleeve 108, a flexible pad is utilized which contains the sensor which is configured and adapted to transition between furled and unfurled states through mechanical and/or electro-mechanical means. The pad can be rolled up and inserted through a cannula, then unrolled by a grasper. It can then be removed by pulling it back through a cannula with a grasper.

In one application, the sensor can be wrapped around anastomosed tissue to take a measurement of the entire staple line of the anastomosis.

Figure 4:
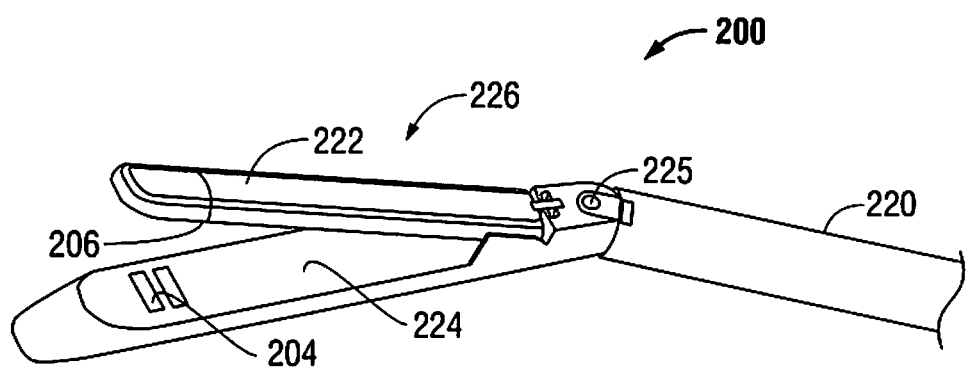
FIG. 4 is a perspective view of an end effector of a surgical instrument illustrating a further embodiment of the present disclosure.

In another embodiment, as shown in FIG. 4, a sensor including photo-detectors and light emitting sources may be operatively coupled into a laparoscopic device. As shown in FIG. 4, an intra-operative sensor device 200 includes an elongated shaft 220 including an end effector 226 disposed at a distal end of the elongated shaft 220 including a pair of jaws 222, 224. One or more light emitting sources 204 may be operatively coupled into one of the jaws 222, 224, and one or more photo-detectors 206 may be operably coupled with one of the jaws 222, 224. As shown in FIG. 4, light emitting sources 204 are positioned on jaw 224, and a photo-detector(s) 206 is operatively coupled into jaw 222. As tissue is grasped between the jaws 222, 224, the light emitting sources 204 illuminate the portion of tissue positioned between the jaws 222, 224. The photo-detector(s) 206 detects the light that is transmitted through the tissue to collect information, including but not limited to, the patient's pulse and oxygenation of the tissue. Thus, in this version, light is detected passing through tissue, rather than backscattered light as in other embodiments described herein.

The end effector 226 of the intra-operative sensor device 200 may be capable of articulation, as shown in FIG. 4. As shown in FIG. 4, the end effector 226 may articulate with respect the elongated shaft 220 about pivot point 225. In addition, jaw 224 of the end effector 226 may be configured and adapted to receive a surgical stapling cartridge, and jaw 222 may be an anvil to effect the formation of staples upon the firing of the device. A knife (not shown) may also be included that travels along the length of the stapling cartridge to cut tissue grasped between the jaws 222, 224. Advantageously, the presence of the optical sensor that is operatively coupled to the end effector 226 facilitates monitoring the condition of the tissue grasped between the jaws 222, 224. Knowledge of the condition, e.g., vascularization, of the tissue grasped may facilitate inhibiting damage to the tissue from further manipulation, e.g., stapling or cutting, of the tissue.

In other embodiments, the light emitting sources and photo-detectors can be incorporated into first and second jaws, respectively, of a grasper or other instrument.

Figure 5:
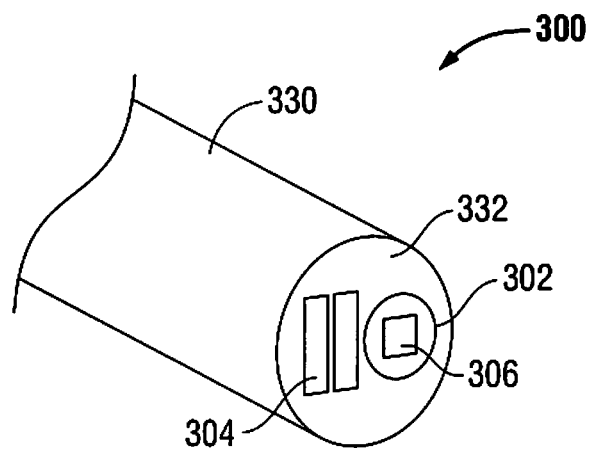
FIG. 5 is a front perspective view of another embodiment of a surgical instrument having an intra-operative sensor device.

An intra-operative sensor device 300, as shown in FIG. 5, is an endoscopic or laparoscopic device that includes an elongated shaft 330 and a distal end 332. One or more light emitting sources 304 and one or more photo-detectors 306 are disposed on the distal end 332. An optical isolator ring 302 may be placed around either the one or more light emitting sources 304 or around the one or more photo-detectors 306; in the illustrated embodiment it is placed around photo-detector 306. The intra-operative sensor device 300 may be inserted into a body cavity through a natural orifice or a surgical incision such that measurements may be collected locally on the tissue surface by the backscattering of light reflected by the tissue.

Figure 6:
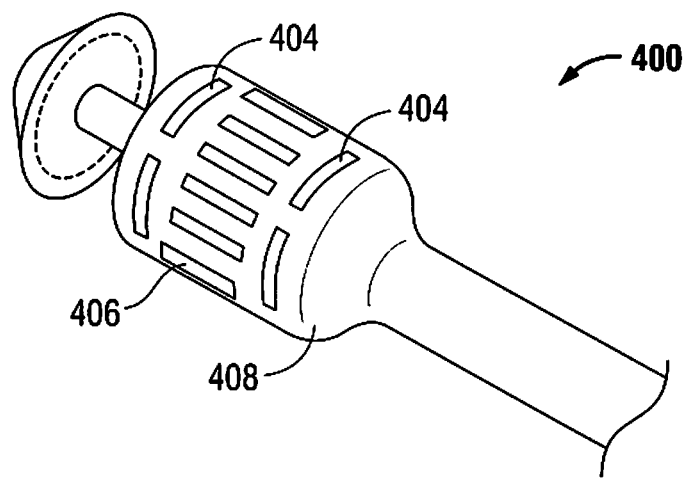
FIG. 6 is a perspective view of yet another embodiment of a surgical instrument having an intra-operative sensor device and showing the distal end portion of the instrument.

An intraoperative sensor device 400 of FIG. 6 is a circular anastomosis instrument with the light emitting sources 404 arranged around the circumference of the shell assembly 408 which contains a plurality of fasteners. As shown, a series of photo-detectors 406 are arranged around the circumference of the shell assembly 408, with some of the light emitting sources 404 located proximal of the photo-detectors 406 and some located distal of the photo-detectors 406. It is also contemplated that the arrangement can be reversed, so that light emitting sources are positioned between a distal arrangement of photo-detectors and a proximal arrangement of photo-detectors.

It should be appreciated hat the sensor arrangements can be placed on the laparascopic/endoscopic staplers, open staplers which apply linear rows of fasteners, laparoscopic or open energy devices, laparoscopic grasping tools, as well as other instruments. The sensors can be provided built into the device, or alternatively, can be a separate unit and attached to the device.

It will be understood by those skilled in the art that various modifications and changes in form and detail may be made herein without departing from the scope and spirit of the present disclosure.

What is claimed is:

1. An intra-operative sensor device for detecting tissue or body parameters comprising:
   at least one light emitting source;
   at least one photo-detector, wherein an optical isolator ring is placed around either the at least one light emitting source or the at least one photo-detector; and
   an inflatable sleeve including the at least one light emitting source and the at least one photo-detector mounted thereon, the inflatable sleeve transitionable between a furled state and an unfurled state.

2. The intra-operative sensor device of claim 1, wherein the at least one photo-detector is placed within the optical isolator ring, and the at least one light emitting source surrounds the optical isolator ring.

3. The intra-operative sensor device of claim 1, wherein injection of inflation fluid into the inflatable sleeve transitions the inflatable sleeve to the unfurled state.

4. The intra-operative sensor device of claim 1, wherein the inflatable sleeve is biased toward the furled state.

5. The intra-operative sensor device of claim 1, wherein the inflatable sleeve is adapted and configured to be wrapped around the tissue.

6. An intra-operative sensor device for detecting tissue or body parameters comprising:
   at least one photo-detector;
   at least one light emitting source spaced radially from the at least one photo-detector, the at least one photo-detector detecting light backscattered from light emitted by the at least one light emitting source to detect parameters of the tissue or the body; and
   an inflatable sleeve including the at least one light emitting source and the at least one photo-detector mounted thereon, the inflatable sleeve transitionable between a furled state and an unfurled state.

7. The intra-operative sensor device of claim 6, wherein the at least one light emitting source substantially encircles the at least one photo-detector.

8. The intra-operative sensor device of claim 7, further comprising an optical isolator ring positioned between the at least one photo-detector and the at least one light emitting source.

9. The intra-operative sensor device of claim 6, wherein the inflatable sleeve is biased toward one of the furled state or the unfurled state.

* * * * *